(12) United States Patent
Shimizu et al.

(10) Patent No.: US 7,125,378 B2
(45) Date of Patent: Oct. 24, 2006

(54) HERMETICALLY SEALED IMAGING SYSTEM FOR MEDICAL APPLICATIONS

(75) Inventors: Masami Shimizu, Hachioji (JP);
Masahiro Hagihara, Hachioji (JP);
Masaki Takayama, Hachioji (JP);
Satoshi Takekoshi, Hachioji (JP);
Nobuaki Akui, Hino (JP); Kazuo Banju, Hachioji (JP); Ichiro Ikari, Hachioji (JP); Hiroyuki Kuroda, Hachioji (JP)

(73) Assignee: Olympus Corporation, Tokyo (JP)

( * ) Notice: Subject to any disclaimer, the term of this patent is extended or adjusted under 35 U.S.C. 154(b) by 88 days.

(21) Appl. No.: 10/643,174

(22) Filed: Aug. 18, 2003

(65) Prior Publication Data

US 2004/0210108 A1    Oct. 21, 2004

(30) Foreign Application Priority Data

Aug. 22, 2002   (JP)   ............................. 2002-242399

(51) Int. Cl.
*A61B 1/04* (2006.01)
*H04N 7/18* (2006.01)

(52) U.S. Cl. .................. 600/112; 600/109; 600/110; 600/133; 600/167; 348/73

(58) Field of Classification Search ................ 600/112, 600/109, 110, 133, 167; 348/73, 75
See application file for complete search history.

(56) References Cited

U.S. PATENT DOCUMENTS

| | | | |
|---|---|---|---|
| 5,225,941 A | 7/1993 | Saito et al. | |
| 5,490,015 A | 2/1996 | Umeyama et al. | |
| 5,836,867 A | 11/1998 | Speier et al. | |
| 5,842,972 A | 12/1998 | Wulfsberg | |
| 5,876,327 A * | 3/1999 | Tsuyuki et al. | 600/112 |
| 5,895,350 A * | 4/1999 | Hori | 600/167 |
| 6,030,339 A * | 2/2000 | Tatsuno et al. | 600/112 |
| 6,080,101 A * | 6/2000 | Tatsuno et al. | 600/112 |
| 6,292,221 B1 * | 9/2001 | Lichtman | 348/345 |
| 6,464,631 B1 * | 10/2002 | Girke et al. | 600/109 |
| 6,529,232 B1 * | 3/2003 | Kraas et al. | 348/65 |
| 6,572,539 B1 * | 6/2003 | Akiba | 600/167 |
| 6,743,168 B1 * | 6/2004 | Luloh et al. | 600/167 |
| 6,805,665 B1 * | 10/2004 | Tatsuno et al. | 600/112 |
| 6,855,106 B1 * | 2/2005 | May et al. | 600/112 |

FOREIGN PATENT DOCUMENTS

| | | |
|---|---|---|
| DE | 196 31 840 A1 | 2/1998 |
| JP | 10-127568 | 5/1998 |
| JP | 2000-287914 | 10/2000 |
| JP | 2002-112956 | 4/2002 |
| WO | WO 01/41631 A1 | 6/2001 |

* cited by examiner

*Primary Examiner*—John P. Leubecker
(74) *Attorney, Agent, or Firm*—Scully, Scott, Murphy & Presser, P.C.

(57) ABSTRACT

An imaging system includes: an optical-system holding member for holding an optical system to form an optical image of a subject; an imaging-device holding member for holding an imaging device to obtain the optical image formed by the optical system; a case for hermetically enclosing the optical-system holding member and the imaging-device holding member; a hermetic connector for hermetically sealing the case, the hermetic connector being electrically connected to the imaging device; a power generator for generating a driving force to move either of the optical-system holding member and the imaging-device holding member; and a driving-force transfer member for connecting the power generator and either the optical-system holding member or the imaging-device holding member to transfer the driving force of the power generator to either the optical-system holding member or the imaging-device holding member.

19 Claims, 7 Drawing Sheets

HERMETICALLY SEALED IMAGING SYSTEM FOR MEDICAL APPLICATIONS

This application claims benefit of Japanese Application No. 2002-242399 filed in Japan on Aug. 22, 2002, the contents of which are incorporated by this reference.

BACKGROUND OF THE INVENTION

1. Field of the Invention

The present invention relates to an imaging system capable of being subjected to autoclave sterilization (high-pressure and high-temperature steam sterilization).

2. Description of Related Art

Imaging systems are used in optical endoscopes and electronic endoscopes. The imaging systems are capable of obtaining an optical image of a subject to form an endoscopic image, and displaying the image on a monitor or storing the image to an image recording device.

Such an imaging system includes an optical system for forming an optical image of a subject and an imaging device such as a CCD (charge coupled device) for obtaining the optical image formed through the optical system.

The imaging system requires the alignment between the optical system and the imaging device in order to obtain a favorable optical image of a subject. For the alignment between the optical system and the imaging device, the alignment therebetween is performed along the optical axis with respect to a focal length (focus adjustment) or the alignment therebetween is performed in the direction perpendicular to the optical axis.

Generally, the imaging system for endoscope needs cleaning and disinfecting after endoscopy. In addition, recently, the imaging system requires sterilization to prevent infections. The imaging system uses a low-cost sterilizing method for exposing an object to be sterilized in high-temperature and high-pressure steam for a predetermined period, the method being called autoclave sterilization. Accordingly, the optical system and the imaging device have to be hermetically sealed to allow the imaging system to exhibit resistance to the autoclave sterilization.

For example, Japanese Unexamined Patent Application Publication No. 2002-112956, to the same assignee as this application, discloses an imaging system for adjusting the focus of an optical system using magnetic connection.

PCT Japanese Translation Patent Publication No. WO 01/41631 A1, to the same assignee as this application, discloses an imaging system for adjusting a focus using an actuator in addition to the foregoing magnetic connection. Further, U.S. Pat. No. 5,490,015, to the same assignee as this application, discloses an imaging system for adjusting a focus using a piezoelectric element.

German Patent No. DE 19631840 A1 discloses an imaging system including a movable optical system in an airtight case. In the imaging system, a control section disposed in the housing is operated from the outside of a deformable wall region to vary the optical performance (a focal length) in airtight condition.

U.S. Pat. No. 5,225,941 discloses a driving device for an imaging system. In the driving device, an optical system is driven along the optical axis by frictional engagement with a shaft vibrated due to the expansion and contraction of a piezoelectric element.

U.S. Pat. No. 5,836,867 discloses a magnetic coupling assembly for an imaging system. In the assembly, the optical performance (a focal length) can be varied in airtight condition due to the magnetic coupling.

SUMMARY OF THE INVENTION

Accordingly, it is an object of the present invention to provide an imaging system including: an optical-system holding member for holding an optical system to form an optical image of a subject; an imaging-device holding member for holding an imaging device to obtain the optical image formed by the optical system; a case for hermetically enclosing the optical-system holding member and the imaging-device holding member; a hermetic connector for hermetically sealing the case, the hermetic connector being electrically connected to the imaging device; a power generator for generating a driving force to move either the optical-system holding member or the imaging-device holding member; and a driving-force transfer member for connecting the power generator and either the optical-system holding member or the imaging-device holding member to transfer the driving force of the power generator to either the optical-system holding member or the imaging-device holding member.

Another object of the present invention is to provide an imaging system including: an optical system for forming an optical image of a subject; an imaging device for obtaining the optical image formed by the optical system; a case for enclosing the optical system and the imaging device; a hermetic connector for hermetically sealing the case, the hermetic connector being electrically connected to the imaging device; a holding member for holding the optical system so that the optical system is movable forward and backward along the optical axis relative to the imaging device, the holding member being disposed in the case; a power generator for generating a driving force to move the holding member; and a driving-force transfer member for connecting the power generator and the holding member to transfer the driving force of the power generator to the holding member.

Still another object of the present invention is to provide an imaging system including: an optical system for forming an optical image of a subject; an imaging device for obtaining the optical image formed by the optical system; a case for enclosing the optical system and the imaging device; a hermetic connector for hermetically sealing the case, the hermetic connector being electrically connected to the imaging device; a holding member for holding the optical system so that the optical system is movable forward and backward along the optical axis relative to the imaging device, the holding member being disposed in the case; a power generator for generating a driving force to move the holding member on the basis of electric energy which is supplied through the hermetic connector; and a driving-force transfer member for connecting the power generator and the holding member to transfer the driving force of the power generator to the holding member.

Other features and advantages of the present invention will become more apparent from the following description.

DETAILED DESCRIPTION OF THE PREFERRED EMBODIMENTS

Embodiments of the present invention will be described hereinbelow with reference to the drawings.

First Embodiment

Figure 1:
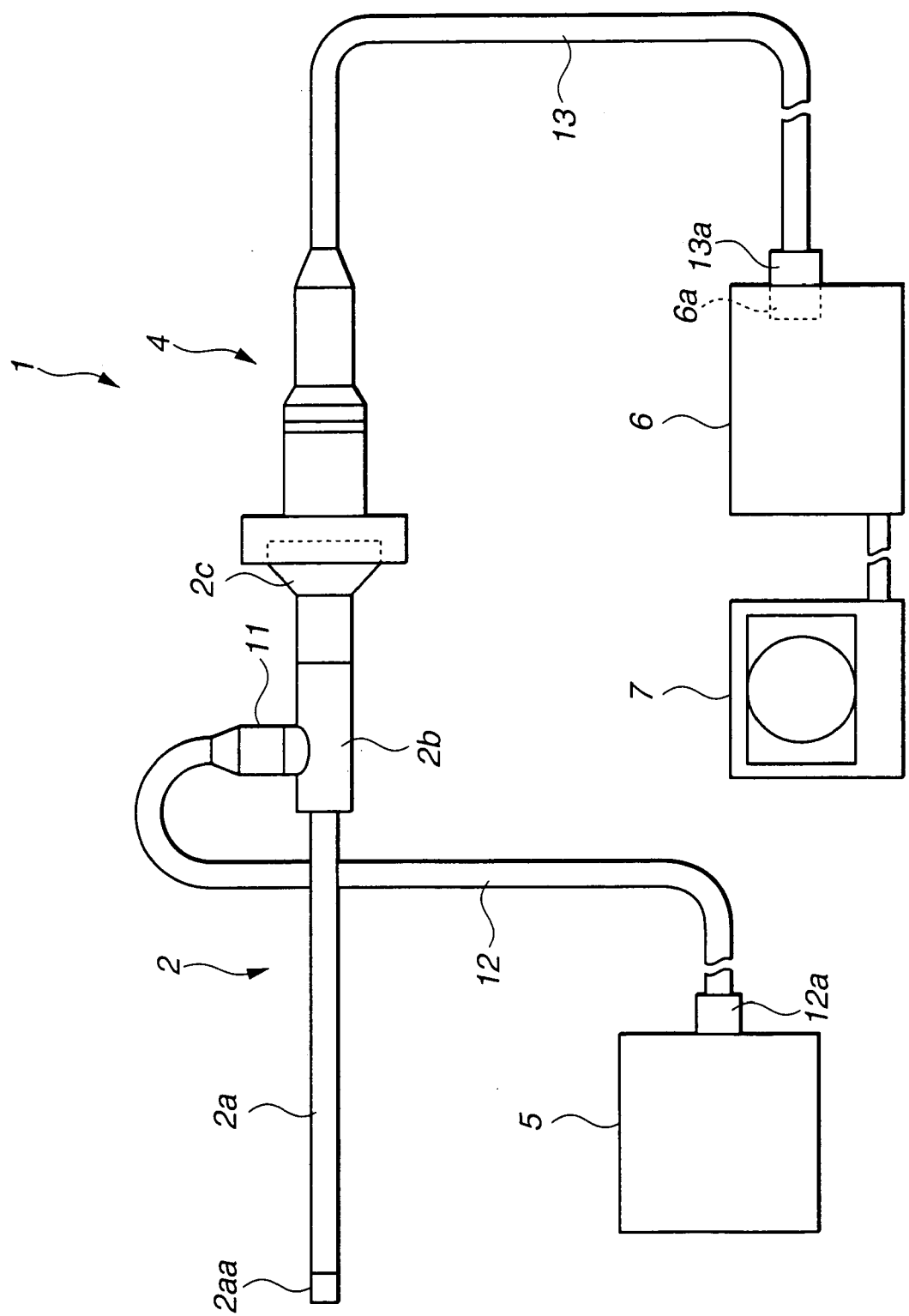
FIG. 1 is a diagram showing the whole structure of an endoscope system comprising an imaging system according to a first embodiment.
Figure 2:
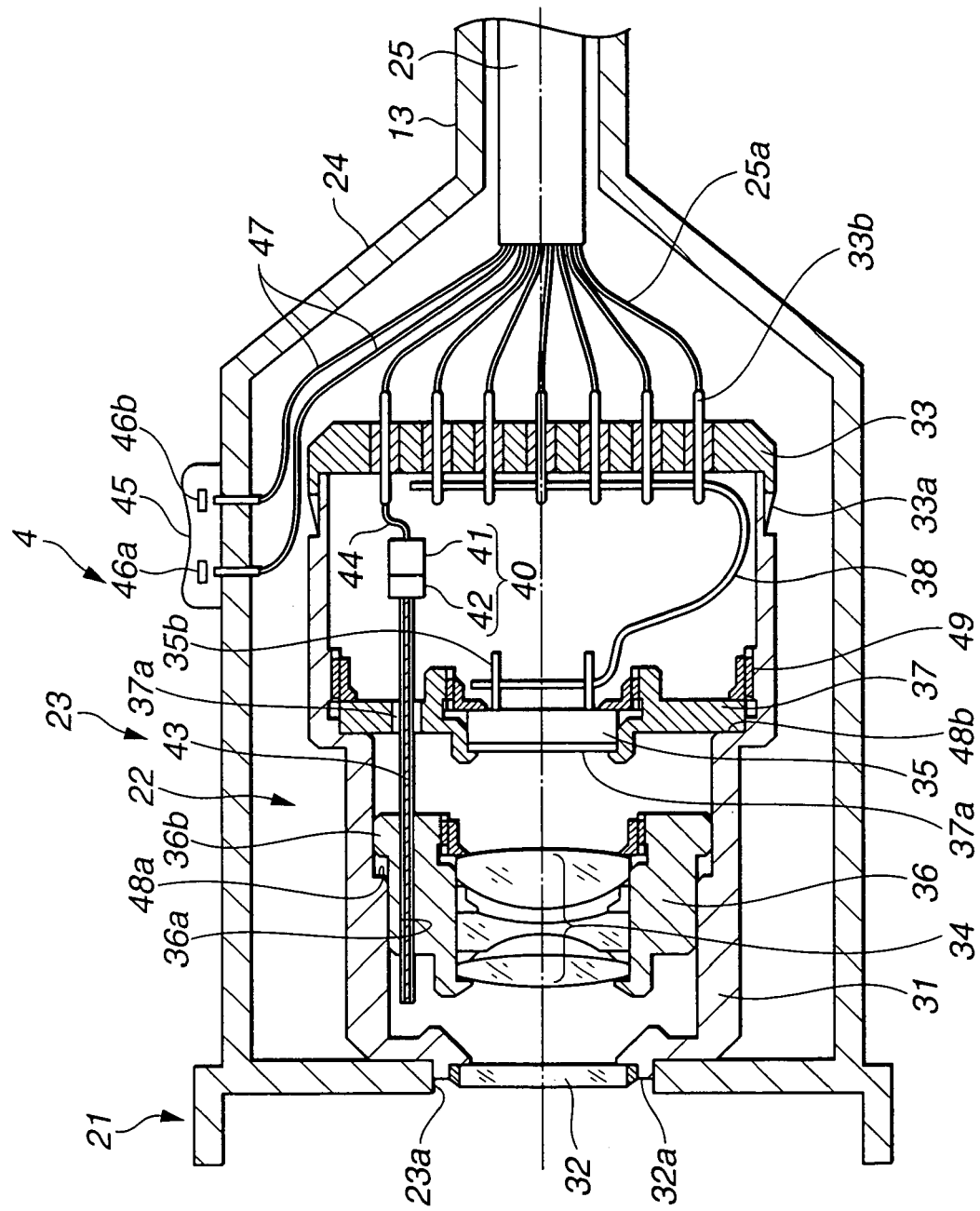
FIG. 2 is a sectional view of the structure of the imaging system of FIG. 1.

FIGS. 1 and 2 illustrate a first embodiment of the present invention.

Referring to FIG. 1, according to the first embodiment, an endoscope system 1 comprises: an optical endoscope (hereinbelow, simply referred to as an endoscope) 2 having a long inserting portion 2a; an imaging system 4 serving as a camera head having an imaging device, which will be described later, the imaging system 4 being detachable from the endoscope 2; a light source 5 for supplying illumination light to the endoscope 2; a camera control unit (hereinbelow, abbreviated to a CCU) 6 for processing a signal of the imaging system 4; and a monitor 7 for receiving a video signal generated from the CCU 6 and displaying an endoscopic image.

According to the present embodiment, the endoscope system 1 uses the (optical) endoscope 2 and includes the imaging system 4 serving as the camera head which is detachable from the (optical) endoscope 2. The endoscope system can also comprise an electronic endoscope (not shown) having a hermetic unit, which will be described later, including an imaging system at the distal end of the inserting portion 2a.

The endoscope 2 comprises the inserting portion 2a, a thick grip 2b extending from the rear end of the inserting portion 2a, and an eyepiece 2c arranged at the rear end of the grip 2b.

For the endoscope 2, a light guide cable 12 is connected to a cap 11 arranged on the side surface of the grip 2b. A detachable connector 12a disposed at the end of the light guide cable 12 can be connected to the light source 5.

White light generated by a lamp (not shown) in the light source 5 is supplied to an incident end surface of the light guide cable 12 and is then transferred through the light guide cable 12 to illuminate a subject through an illumination window (not shown) at a distal end 2aa of the inserting portion 2a of the endoscope 2.

An optical image of the subject illuminated is formed by an objective optical system (not shown) provided for the distal end 2aa of the inserting portion 2a. An incident plane is arranged at the image forming position of the objective optical system. For example, the formed optical image of the subject is incident on an image transfer unit of a relay optical system (not shown) and is then transferred to the eyepiece 2c through the image transfer unit.

The transferred optical image of the subject generated from the image transfer unit is incident on an eyepiece optical system provided for the eyepiece 2c. The optical image can be enlarged and observed as an endoscopic image through an eyepiece window (not shown).

In the endoscope 2, the imaging system 4 is detachable from the eyepiece 2c. A plug 13a, arranged at the end of a camera cable 13 extending from the rear end of the imaging system 4, is detachable from a receptacle 6a of the CCU 6.

The imaging system 4 has an observation window, which will be described later, such that the observation window faces the eyepiece window of the eyepiece 2c, and an imaging optical system disposed at the rear of the observation window. The imaging system 4 has the imaging device such as a CCD on the image forming position of the imaging optical system (refer to FIG. 2).

The imaging device receives driving signals through signal lines arranged in the camera cable 13 to photoelectrically convert an endoscopic image into electric signals. The converted electric signals are read and transferred to the CCU 6. The CCU 6 converts the electric signals into standard video signals. The monitor 7 receives the video signals to display the endoscopic image.

The specific structure of the endoscope imaging system 4 according to the present invention will now be described with reference to FIG. 2.

The imaging system 4 comprises a scope mounting portion 21 which is detachable from the eyepiece 2c of the endoscope 2, and a camera head body 23 having therein a hermetically-sealing unit (hereinbelow, simply referred to as a hermetic unit) 22 on the rear of the scope mounting portion 21. The scope mounting portion 21 and the camera head body 23 are integrated into an housing 24.

The camera cable 13 extends from the rear end of the camera head body 23 and includes a signal cable 25 comprising a bundle of signal lines 25a. The respective signal lines 25a of the signal cable 25 reach the plug 13a and connect thereto.

In the imaging system 4, the scope mounting portion 21 is separated from the camera head body 23 through a partition wall. The partition wall has a hole 23a. The end of the hermetic unit 22 is fitted in the hole 23a so that the hermetic unit 22 is held in the camera head body 23.

For the hermetic unit 22, a hermetic case 31 serves as a case and constitutes a unit body. In the hermetic unit 22, a cover glass 32 serving as an observation window, through which an endoscopic image (optical image of a subject) is obtained, is hermetically attached to the front end of the hermetic case 31 by soldering. The cover glass 32 is made of sapphire exhibiting heat-resisting properties. The periphery of the cover glass 32 is metallized.

A joint 32a of the hermetic unit 22, on which the cover glass 32 is attached, is fitted into the hole 23a of the partition wall, so that the cover glass 32 is arranged in the camera head body 23 so as to be exposed in the hole 23a of the partition wall.

A hermetic connector 33 is airtightly connected to an SO portion 33a at the rear end of the hermetic case 31 by soldering or welding, thus hermetically sealing the hermetic unit 22. The hermetic connector 33 is constructed in such a manner that rod-like metal connecting pins 33b are arranged in respective through-holes formed in the connector 33 and a clearance between each through-hole and the corresponding connecting pin 33b is sealed with molten glass.

The hermetic unit 22 is hermetically sealed by the cover glass 32 and the hermetic connector 33.

Thus, the internal space of the hermetic unit 22 can be hermetically sealed. Therefore, the imaging system 4 can be subjected to autoclave sterilization.

The respective ends of the connecting pins 33b project from the hermetic unit 22. These ends of the connecting pins 33b are connected to the respective ends of the signal lines 25a of the signal cable 25 arranged in the camera cable 13. Thus, the hermetic connector 33 is electrically connected to the plug 13a through the signal lines 25a.

At the rear of the cover glass 32, the hermetic unit 22 has an imaging optical system 34 for forming an endoscopic image captured through the cover glass 32 and an imaging device 35 such as a CCD for obtaining the endoscopic image at the image forming position of the imaging optical system 34.

The imaging optical system 34 comprises at least one group of lenses. The imaging optical system 34 is fixed to a lens frame 36 serving as an imaging-optical-system holding member. The group of lenses can include a group of variable power lenses for zooming and focus adjustment, the lenses being capable of varying the size of an endoscopic image (optical image of a subject).

On the other hand, the imaging device 35 is fixed to an imaging-device frame 37 serving as an imaging-device holding member. Leads 35*b* extend from the rear of an imaging surface 35*a* of the imaging device 35. The leads 35*b* are connected to a flexible electric board (hereinbelow, referred to as a flexible board) 38 such as a flexible printed circuit (FPC). The flexible board 38 is connected to the connecting pins 33*b* for imaging in the hermetic connector 33.

According to the present embodiment, the hermetic unit 22 is constructed so that the lens frame 36 holding and fixing the imaging optical system 34 is movable (forward and backward) along the optical axis.

In other words, the hermetic unit 22 includes a motor unit 40 for moving the lens frame 36 along the optical axis. The motor unit 40 is disposed between the imaging-device frame 37 and the hermetic connector 33. The motor unit 40 comprises a motor 41 such as a DC motor for generating an output of rotational motion, and a reduction gear 42 which is connected to the motor 41 to control the number of revolutions of the motor 41 at predetermined proper speed. The motor unit 40 is fixed to the hermetic case 31 using a fixing member (not shown).

The motor unit 40 also includes a feed screw 43 which is operatively associated with the rotation of the reduction gear 42. The feed screw 43 is mechanically coupled with the reduction gear 42. The feed screw 43 is disposed through a through-hole 37*a* formed in the imaging-device frame 37 and is engaged with a screw hole 36*a* formed in the lens frame 36.

In other words, the hermetic unit 22 according to the present embodiment is constructed in such a manner that the motor unit 40 functions as a power generator for generating a driving force to move the lens frame 36 along the optical axis, and the feed screw 43 is mechanically coupled to the motor unit 40 through the screw hole 36*a* in the lens frame 36 to transfer the rotational motion generated in the motor unit 40 to the lens frame 36, namely, the feed screw 43 functions as a driving-force transfer member.

A motor harness 44 extends from the rear of the motor 41. The motor harness 44 is electrically connected to the connecting pin 33*b* for the motor in the hermetic connector 33. The motor 41 receives a driving signal through the signal line 25*a* from a drive circuit (not shown) disposed in the CCU 6 or the plug 13*a*. Thus, the motor 41 is driven.

The drive circuit rotates the motor 41 forward and backward (flexibly) in accordance with inputs supplied from a control switch 45 such as a seesaw switch disposed on the outer surface of the camera head body 23.

The control switch 45 has at least two contacts 46 (contacts 46*a* and 46*b*). Control-switch harnesses 47 extending from the control switch 45 are arranged in the camera cable 13 to electrically connect the control switch 45 to the drive circuit.

For example, when the control switch 45 is operated so that power is supplied to the contact 46*a*, the control switch 45 controls the drive circuit to rotate the motor 41 forward. On the other hand, when the control switch 45 is operated so that power is supplied to the contact 46*b*, the control switch 45 controls the drive circuit to rotate the motor 41 backward.

For the motor unit 40, in response to the forward or backward rotation of the motor 41, the reduction gear 42 allows the feed screw 43 to rotate forward or backward (flexibly). Due to the operation of the screw hole 36*a* engaged with the feed screw 43, the lens frame 36 moves (forward or backward) along the optical axis to adjust the focus.

The outer surface of the lens frame 36 serves as a slid contact surface which is slidable on the inner wall of the hermetic case 31. A protrusion 36*b* on the outer surface of the lens frame 36 is come into contact with a contact portion 48*a* on the inner wall of the hermetic case 31, thus restricting the movement of the lens frame 36 toward the endoscope 2 along the optical axis. The rear end, including the protrusion 36*b*, of the lens frame 36 is come into contact with the imaging-device frame 37, thus restricting the movement of the lens frame 36 toward the imaging device 35 along the optical axis. The outer periphery of the imaging-device frame 37 is fixed to a contact portion 48*b* on the inner wall of the hermetic case 31 using a fixing member 49.

The detachable imaging system 4 according to the present embodiment with the above structure is attached to the eyepiece 2*c* of the endoscope 2 and is then used in endoscopy.

An endoscopic image captured through the endoscope 2 is transferred to the imaging device 35 through the cover glass 32 and the imaging optical system 34.

The imaging device 35 photoelectrically converts the endoscopic image into electric signals and then transmits the signals to the CCU 6 through the flexible board 38, the hermetic connector 33, the signal lines 25*a*, the plug 13*a*, and the receptacle 6*a*. The CCU 6 converts the electric signals into video signals and then allows the monitor 7 to display the endoscopic image.

When the endoscopic image displayed on the monitor 7 is out of focus, the user operates the control switch 45 to adjust the focus. A case where the lens frame 36 is moved (forward) toward the imaging device 35 will now be described.

The user operates the control switch 45 so that power is applied to the contact 46*a*. Then, the control switch 45 generates a forward-rotation signal, caused by energizing the contact 46*a*, to the drive circuit. The drive circuit receives the forward-rotation signal and then allows the motor 41 to rotate forward.

A driving signal generated from the drive circuit is transmitted to the motor 41 through the signal lines 25*a*, the hermetic connector 33, and the motor harness 44, thus rotating the motor 41 forward. Simultaneously, the reduction gear 42 reduces the number of revolutions of the motor 41. The reduced (rotational) power of the motor 41 allows the feed screw 43 to rotate forward.

When the feed screw 43 rotates, the lens frame 36 is moved toward the imaging device 35 due to the operation of the screw hole 36*a* engaged with the feed screw 43, thus adjusting the focus. In this instance, the moving speed of the lens frame 36 is determined on the basis of the gear ratio between the motor 41 and the reduction gear 42. The gear ratio between the motor 41 and the reduction gear 42 is set so that the moving speed of the lens frame 36 is optimized.

On the other hand, when the user wants to move the lens frame 36 toward the endoscope 2, the user operates the control switch 45 so that power is supplied to the contact 46b, so that the motor 41 and the feed screw 43 are rotated backward in a manner similar to the above.

According to the present embodiment, therefore, the imaging system 4 can adjust the focus with reliability. The operability of the imaging system 4 is good. The imaging system 4 can be subjected to autoclave sterilization.

According to the present embodiment, the imaging system 4 can also use a group of variable power lenses for zooming and focus adjustment as the group of lenses of the imaging optical system 34. Accordingly, zooming and focusing can be easily performed with reliability.

According to the present embodiment, the imaging system 4 is constructed so that either of the lens frame 36 and the imaging-device frame 37 is movable (forward and backward). The present invention is not limited to this case. The imaging system 4 can also be constructed so that both of the lens frame 36 and the imaging-device frame 37 are movable (forward and backward).

According to the present embodiment, the imaging system 4 has the imaging optical system 34 and the imaging device 35 in one hermetic unit 22. The present invention is not limited to this case. The imaging optical system 34 and the imaging device 35 can be disposed as separate components, for example, the imaging optical system 34 is included in an optical adapter and the imaging device 35 is included in a camera head. The imaging system 4 can also comprise the optical adapter and the camera head.

In this case, connecting the optical adapter and the camera head uses a known technique such as engagement with a screw. Electrically connecting the optical adapter and the camera head also uses a known technique. For example, electric contacts are provided for the optical adapter and the camera head, respectively.

Second Embodiment

Figure 3:
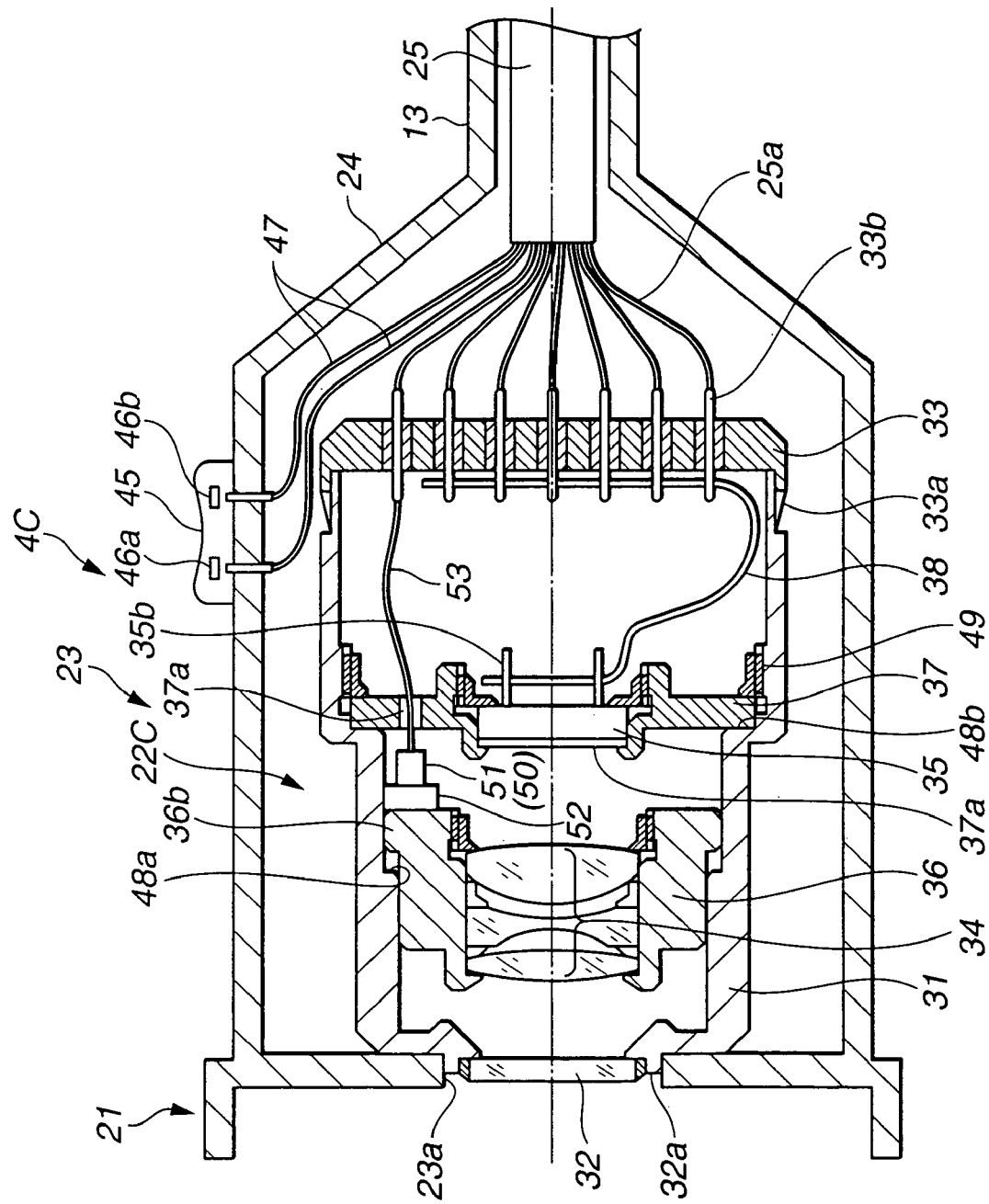
FIG. 3 is a sectional view of the structure of an imaging system according to a second embodiment.

FIG. 3 illustrates a second embodiment of the present invention.

According to the second embodiment, a piezoelectric unit is used instead of the motor unit 40 as a power generator. The other components are the same as those of the first embodiment and the description thereof is omitted. The second embodiment will now be described using the same components designated by the same reference numerals as those of the first embodiment.

Referring to FIG. 3, an imaging system 4C according to the second embodiment has a piezoelectric unit 50 for moving the lens frame 36 (forward and backward) along the optical axis. The piezoelectric unit 50 is provided for the lens frame 36.

The piezoelectric unit 50 comprises at least one piezoelectric element 51. The piezoelectric unit 50 connects one end of the piezoelectric element 51 to the lens frame 36 using a connecting member 52.

The piezoelectric unit 50 uses the expansion and contraction of the piezoelectric element 51 based on an applied voltage and also uses a frictional fitting force of the lens frame 36 or the connecting member 52 to move the lens frame 36 (forward and backward) along the optical axis.

A harness 53 used for the piezoelectric element extends from the rear end of the piezoelectric element 51. The piezoelectric-element harness 53 is arranged through the through-hole 37a in the imaging-device frame 37 and is electrically connected to the connecting pin 33b used for the piezoelectric element, the connecting pin 33b being disposed in the hermetic connector 33. A driving voltage is transferred from a driving-voltage generating circuit (not shown), disposed in the CCU 6 or the plug 13a, to the piezoelectric element 51 through the signal line 25a and is then applied to the piezoelectric element 51.

The lens frame 36 or the connecting member 52 has a slide contact portion which is frictionally fitted on the inner wall of the hermetic case 31 with a predetermined proper frictional force. More specifically, the slide contact portion on the outer surface of the lens frame 36 or the connecting member 52 is slidable on the inner wall of the hermetic case 31 with the predetermined proper frictional force.

In other words, according to the present embodiment, a hermetic unit 22B is constructed in such a manner that the piezoelectric unit 50 functions as a power generator for generating a driving force to move the lens frame 36 along the optical axis, and the connecting member 52 is mechanically coupled with the connecting member 52 to transfer the expansion and contraction caused in the piezoelectric unit 50 to the lens frame 36, namely, the connecting member 52 functions as a driving-force transfer member. The piezoelectric unit 50 is fixed to the hermetic case 31 using a fixing member (not shown).

The protrusion 36b on the outer surface of the lens frame 36 is come into contact with the contact portion 48a on the inner wall of the hermetic case 31, thus restricting the movement of the lens frame 36 toward the endoscope 2 along the optical axis. The outer periphery of the imaging-device frame 37 is fixed to the contact portion 48b on the inner wall of the hermetic case 31 using the fixing member 49.

The CCU 6 or the plug 13a has therein the driving-voltage generating circuit (not shown) for driving the piezoelectric element 51. In the same way as the first embodiment, in accordance with an input supplied from the control switch 45, the voltage waveform of an output driving voltage is changed to expand or contract the piezoelectric element 51.

In accordance with the voltage waveform of the driving voltage generated from the driving-voltage generating circuit, the rate of expansion and contraction of the piezoelectric element 51 and the length thereof are changed. Thus, the moving speed of the lens frame 36 and the moving distance thereof are changed.

The control switch 45 is constructed in a manner similar to the first embodiment and is electrically connected to the driving-voltage generating circuit.

For example, when the control switch 45 is operated so that power is supplied to the contact 46a, the control switch 45 allows the driving-voltage generating circuit to operate so that the piezoelectric element 51 expands. On the other hand, when the control switch 45 is operated so that power is supplied to the contact 46b, the control switch 45 allows the driving-voltage generating circuit to operate so that the piezoelectric element 51 contracts.

The piezoelectric unit 50 is constructed in such a manner that in accordance with the expansion or contraction of the piezoelectric element 51, the connecting member 52 transfers the expansion or contraction of the piezoelectric element 51 to the slide contact portion on the outer surface of the lens frame 36 or the connecting member 52, so that the lens frame 36 and the connecting member 52 are moved (forward or backward) along the optical axis against the frictional force applied to the inner wall of the hermetic case 31, thus adjusting the focus.

The detachable imaging system 4C according to the second embodiment with the above structure is attached to the eyepiece 2c of the endoscope 2 in the same way as the first embodiment and is then used in endoscopy.

When an endoscopic image viewed on the monitor 7 is out of focus, the user operates the control switch 45 to adjust the focus.

The user operates the control switch 45 so that power is supplied to the contact 46a. Then, the control switch 45 outputs an expansion signal, caused by supplying power to the contact 46a, to the driving-voltage generating circuit. When receiving the expansion signal, the driving-voltage generating circuit operates so that the piezoelectric element 51 expands and then generates a driving signal.

The driving signal generated from the driving-voltage generating circuit is transmitted to the piezoelectric element 51 through the signal line 25a, the hermetic connector 33, and the piezoelectric-element harness 53, so that the piezoelectric element 51 expands in response to the voltage waveform of the driving voltage. The connecting member 52 transfers the expansion of the piezoelectric element 51 to the slide contact portion on the outer surface of the lens frame 36 or the connecting member 52. Then, the lens frame 36 and the connecting member 52 move toward the imaging device 35 against the frictional force applied to the inner wall of the hermetic case 31, thus adjusting the focus.

On the other hand, when the user wants to move the lens frame 36 toward the endoscope 2, the user operates the control switch 45 so that power is supplied to the contact 46b to contract the piezoelectric element 51 in response to the voltage waveform of the driving voltage in a manner similar to the above. The lens frame 36 and the connecting member 52 move toward the endoscope 2 against the frictional force applied to the inner wall of the hermetic case 31, thus adjusting the focus.

Consequently, the imaging system 4 according to the second embodiment can obtain the same advantages as those of the foregoing first embodiment.

Third Embodiment

Figure 4:
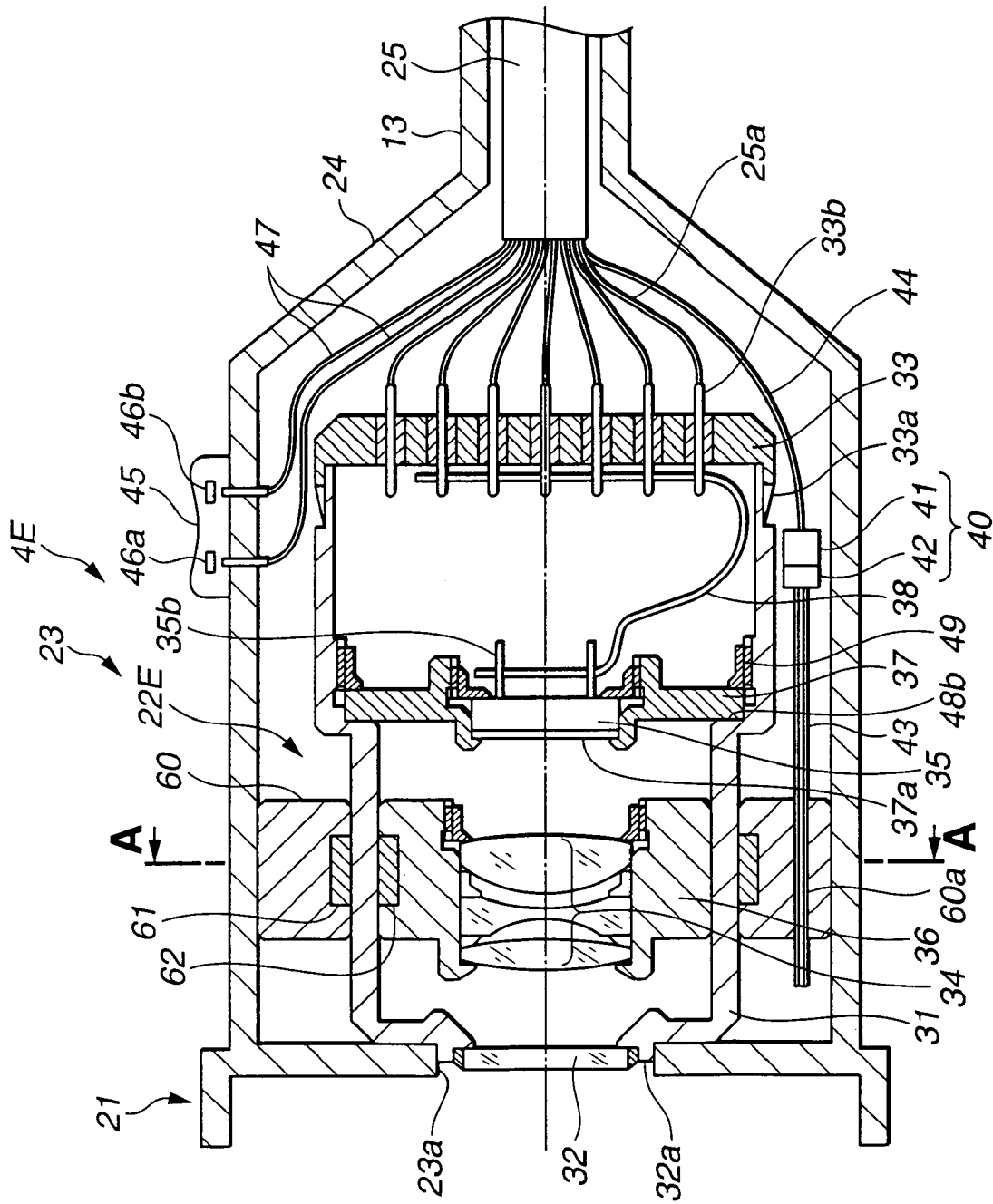
FIG. 4 is a sectional view of the structure of an imaging system according to a third embodiment.
Figure 5:
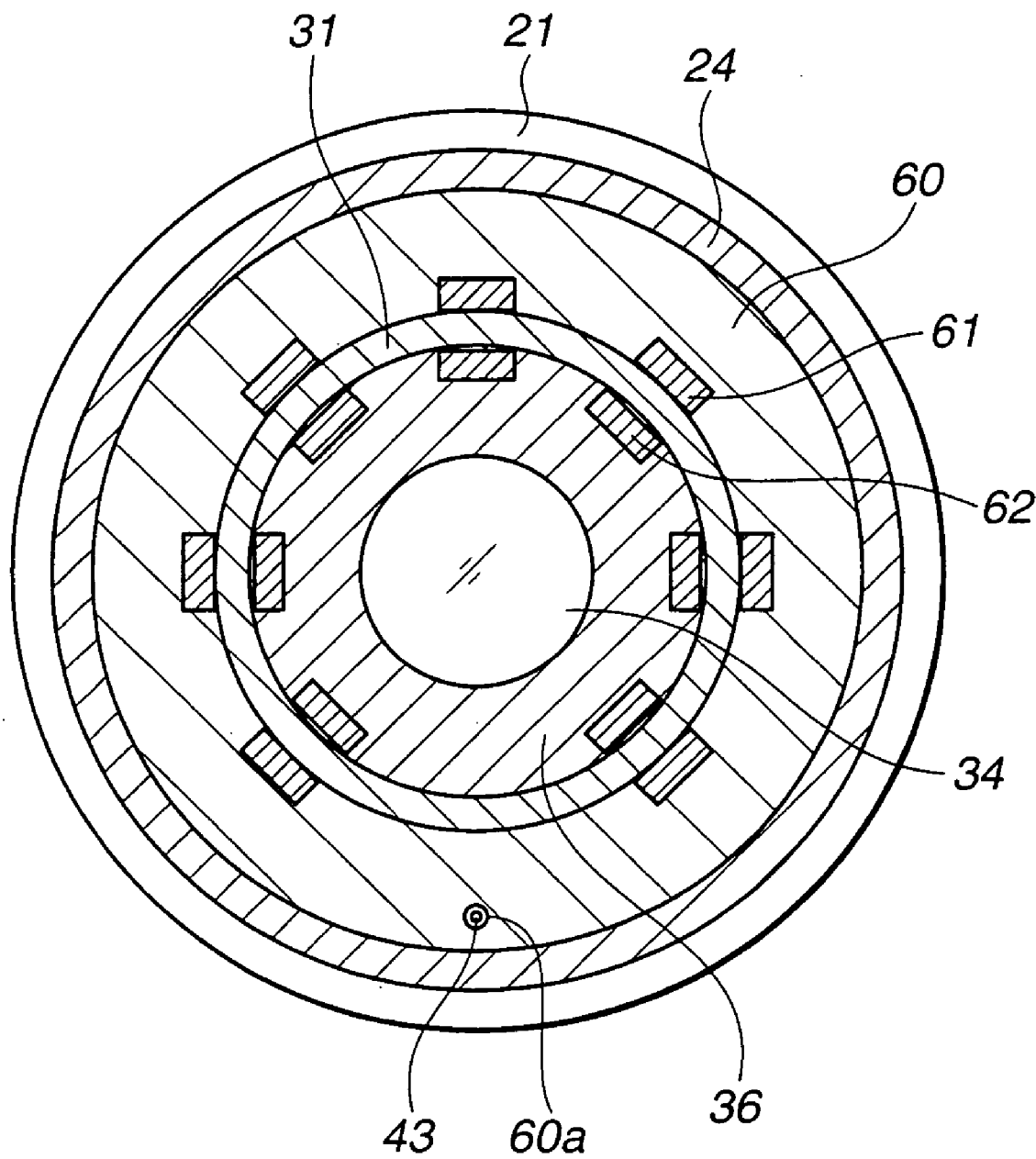
FIG. 5 is a cross-sectional view of the imaging system at the line A—A of FIG. 4.

FIGS. 4 and 5 illustrate a third embodiment of the present invention.

According to the third embodiment, an imaging system is constructed using magnetic coupling between the inside and the outside of a hermetic unit. The other components are the same as those of the first embodiment and the description thereof is omitted. The third embodiment will now be described using the same components designated by the same reference numerals as those of the first embodiment.

Referring to FIG. 4, an imaging system 4E according to the third embodiment is constructed in such a manner that the motor unit 40, which is substantially the same as that described in the first embodiment, is disposed between a hermetic unit 22E and the housing 24.

The feed screw 43 provided for the reduction gear 42 of the motor unit 40 is engaged with a screw hole 60a formed in a movable member 60.

Referring to FIG. 5, the movable member 60 has external magnets 61 buried therein. The hermetic unit 22E is constructed such that the lens frame 36 has internal magnets 62 buried therein and the internal magnets 62 are magnetically coupled to the respective external magnets 61 of the movable member 60. Alternatively, the imaging system 4E can have the following structure (not shown). The lens frame 36 is fixed. The internal magnets 62 are buried in the imaging-device frame 37 so that the imaging-device frame 37 is movable along the optical axis.

The detachable imaging system 4E according to the third embodiment with the above structure is attached to the eyepiece 2c of the endoscope 2 in the same way as the above-mentioned embodiment and is then used in endoscopy.

When an endoscopic image viewed on the monitor 7 is out of focus, the user operates the control switch 45 to adjust the focus.

When the user operates the control switch 45, the drive circuit rotates the motor 41 forward or backward in accordance with the operation of the control switch 45 in a manner similar to the first embodiment., thus rotating the feed screw 43 forward or backward.

When the feed screw 43 rotates forward or backward, the movable member 60 having the external magnets 61 therein is moved (forward or backward) along the optical axis by the operation of the screw hole 60a engaged with the feed screw 43.

Then, due to the magnetic coupling with the external magnets 61, the lens frame 36 having the internal magnets 62 therein is moved (forward or backward) along the optical axis, thus adjusting the focus. The reduction gear 42 reduces the rotational speed of the motor 41 in order to move the movable member 60 and the lens frame 36 so that the magnetic coupling between the external magnets 61 and the internal magnets 62 is not disconnected.

Consequently, the imaging system 4E according to the third embodiment can obtain the same advantages as those of the first embodiment.

Fourth Embodiment

Figure 6:
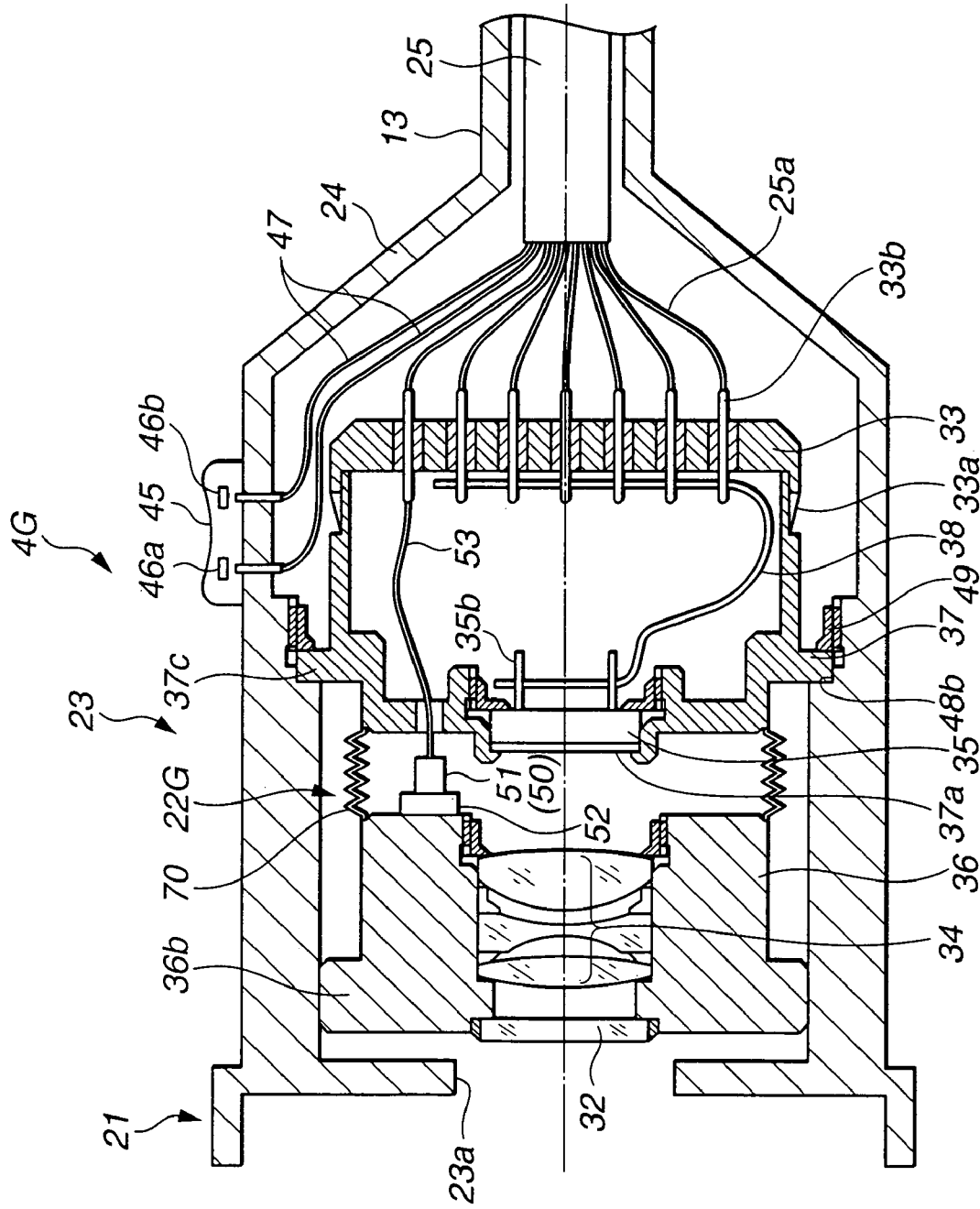
FIG. 6 is a sectional view of the structure of an imaging system according to a fourth embodiment.
Figure 7:
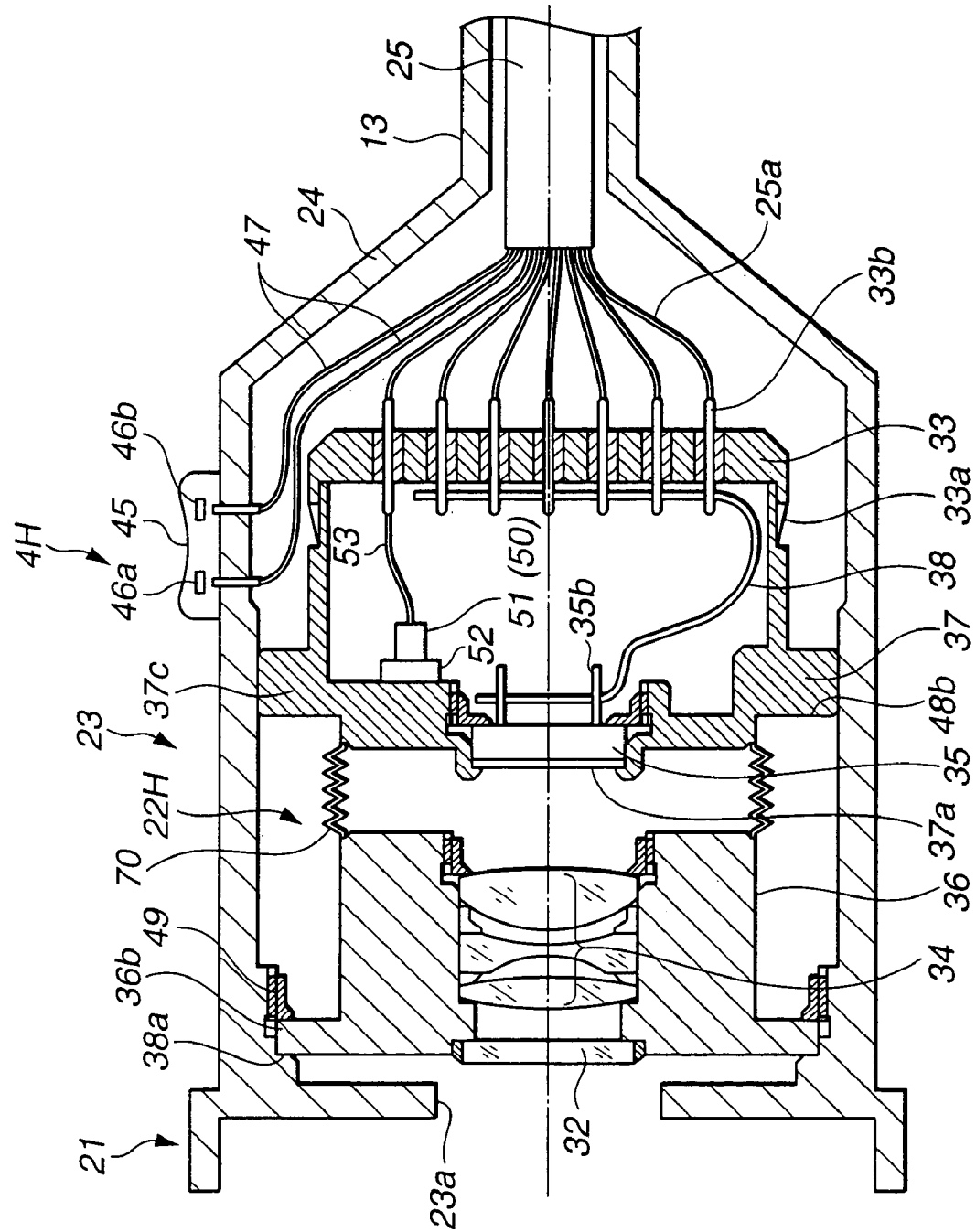
FIG. 7 is a sectional view of the structure of an imaging system as a modification.

FIGS. 6 and 7 illustrate a fourth embodiment of the present invention.

According to the fourth embodiment, a retractable elastic member hermetically connects the lens frame 36 and the imaging-device frame 37 to constitute a hermetic unit which is used instead of the hermetic case 31. Since the other components are the same as those of the second embodiment, the description thereof is omitted. The fourth embodiment will now be described using the same components designated by the same reference numerals as those of the second embodiment.

Referring to FIG. 6, an imaging system 4G according to the fourth embodiment has a retractable bellows 70 instead of the hermetic case 31 as a case. The bellows 70 serves as an elastic member for hermetically connecting the lens frame 36 and the imaging-device frame 37 to constitute a hermetic unit 22G.

The hermetic unit 22G is disposed in the camera head body 23 so that the protrusion 36b on the outer surface of the lens frame 36 is slid on the inner wall of the housing 24 and the lens frame 36 is movable (forward and backward) along the optical axis. The protrusion 36b is fitted on the inner wall of the housing 24 with a predetermined proper frictional force.

The lens frame 36 is connected to the front end of the bellows 70. The lens frame 36 has the same piezoelectric unit 50 as that of the foregoing second embodiment on the rear.

On the other hand, the imaging-device frame 37 is connected to the rear end of the bellows 70. A protrusion 37c on the outer surface of the imaging-device frame 37 is fixed to the contact portion 48b on the inner wall of the housing 24 using the fixing member 49.

The hermetic connector 33 is hermetically connected to the rear end of the imaging-device frame 37 in the same way as the first embodiment.

In the hermetic unit 22G, the bellows 70 controls the lens frame 36 on the basis of the expansion and contraction of the piezoelectric unit 50 so that the lens frame 36 is movable (forward and backward) along the optical axis.

The detachable imaging system 4G according to the fourth embodiment with the above structure is attached to the eyepiece 2c of the endoscope 2 in the same way as the first embodiment and is then used in endoscopy.

When an endoscopic image viewed on the monitor 7 is out of focus, the user operates the control switch 45 to adjust the focus.

The user operates the control switch 45. In response to the operation of the control switch 45, the driving-voltage generating circuit allows the piezoelectric element 51 to expand or contract in accordance with the voltage waveform of a driving voltage in a manner similar to the second embodiment. The bellows 70 contracts or retracts synchronously with the expansion or contraction, so that the lens frame 36 moves (forward or backward) along the optical axis, thus adjusting the focus.

Consequently, the imaging system 4G according to the fourth embodiment can obtain the same advantages as those of the first embodiment.

The imaging system can also be constructed as shown in FIG. 7.

Referring to FIG. 7, an imaging system 4H as a modification has a hermetic unit 22H to permit the imaging-device frame 37 to be movable (forward and backward) along the optical axis.

More specifically, in the hermetic unit 22H, the piezoelectric unit 50 is provided for the imaging-device frame 37. The piezoelectric unit 50 is constructed such that the end of the piezoelectric element 51 is connected to the imaging-device frame 37 by the connecting member 52 so that the imaging-device frame 37 is movable (forward and backward) along the optical axis.

The hermetic unit 22H is constructed in a manner such that due to the expansion or contraction of the piezoelectric unit 50, the bellows 70 controls the imaging-device frame 37 to move (forward or backward) along the optical axis.

The imaging-device frame 37 has a slide contact portion which is fitted on the inner wall of the housing 24 with a predetermined proper frictional force. More specifically, the slide contact portion on the outer surface of the imaging-device frame 37 is slidable on the inner wall of the housing 24 with the predetermined proper frictional force. The protrusion 36b on the outer surface of the lens frame 36 is fixed to the contact portion 38a on the inner wall of the housing 24 using the fixing member 49.

The detachable imaging system 4H according to the modification with the above structure is attached to the eyepiece 2c of the endoscope 2 in the same way as the above-mentioned embodiment and is then used in endoscopy.

When an endoscopic image viewed on the monitor 7 is out of focus, the user operates the control switch 45 to adjust the focus.

When the user operates the control switch 45, in accordance with the operation of the control switch 45, the driving-voltage generating circuit allows the piezoelectric element 51 to expand or contract in response to the voltage waveform of a driving voltage in the same way as the foregoing embodiment. Due to the expansion or contraction thereof, the imaging-device frame 37 moves (forward or backward) along the optical axis to adjust the focus.

Consequently, the imaging system 4H according to the modification can obtain the same advantages as those of the fourth embodiment.

In the present invention, it will be apparent that a wide range of different embodiments can be formed based on this invention without departing from the sprit and scope of the invention. The present invention will be restricted to the appended claims but not be limited to any particular embodiment.

What is claimed is:

1. An imaging system comprising:
an optical-system holding member for holding an optical system to form an optical image of a subject;
an imaging-device holding member for holding an imaging device to obtain the optical image formed by the optical system;
a case for hermetically enclosing the optical-system holding member and the imaging-device holding member, the optical-system holding member and the imaging-device holding member being disposed in the internal space of the case, the optical-system holding member having a slide contact surface which is slidable on the inner wall of the case, a protrusion on the outer surface of the optical-system holding member coming into contact with a contact portion on the inner wall of the case to restrict the forward movement of the optical-system holding member, and the rear end, including the protrusion, of the optical-system holding member coming into contact with the imaging-device holding member to restrict the backward movement thereof along the optical axis;
a hermetic connector for hermetically sealing the case, the hermetic connector being electrically connected to the imaging device;
a power generator for generating a driving force to move either the optical-system holding member or the imaging-device holding member, the power generator being arranged in the case and generating a driving force based on an electric energy supplied thereto via the hermetic connector; and
a driving-force transfer member for connecting the power generator and either the optical-system holding member or the imaging-device holding member to transfer the driving force of the power generator to either the optical-system holding member or the imaging-device holding member.

2. The imaging system according to claim 1, wherein the driving-force transfer member allows the optical-system holding member to be movable forward and backward along the optical axis relative to the imaging-device holding member.

3. The imaging system according to claim 1, wherein the driving-force transfer member allows the imaging-device holding member to be movable forward and backward along the optical axis relative to the optical system holding member.

4. The imaging system according to claim 1, wherein the power generator and the driving-force transfer member are disposed in the case.

5. The imaging device according to claim 4, wherein the power generator includes a motor unit, and the driving-force transfer member mechanically connects to the motor unit to transfer torque of the motor unit.

6. The imaging system according to claim 4, wherein the power generator includes a piezoelectric unit, and the driving-force transfer member mechanically connects to the piezoelectric unit to transfer the expansion and contraction of the piezoelectric unit.

7. An imaging system comprising:
an optical-system holding member for holding an optical system to form an optical image of a subject;
an imaging-device holding member for holding an imaging device to obtain the optical image formed by the optical system;
a case for hermetically enclosing the optical-system holding member and the imaging-device holding member, the optical-system holding member and the imaging-device holding member are connected through a retractable elastic member to constitute the case;
a hermetic connector for hermetically sealing the case, the hermetic connector being electrically connected to the imaging device;
a power generator for generating a driving force to move either the optical-system holding member or the imaging-device holding member, the power generator being arranged in the case and generating a driving force based on an electric energy supplied thereto via the hermetic connector; and
a driving-force transfer member for connecting the power generator and either the optical-system holding member or the imaging-device holding member to transfer the driving force of the power generator to either the optical-system holding member or the imaging-device holding member.

8. The imaging device according to claim 7, wherein the power generator and the driving-force transfer member are disposed in the case.

9. The imaging system according to claim 8, wherein the power generator includes a piezoelectric unit, and the driving-force transfer member mechanically connects to the piezoelectric unit to transfer the expansion and contraction of the piezoelectric unit.

10. The imaging device according to claim 7, wherein the imaging-device holding member has a slide contact surface which is slidable on the inner wall of a housing which encloses the case, and the elastic member restricts the forward or backward movement of the imaging-device holding member along the optical axis.

11. An imaging system comprising:
an optical system for forming an optical image of a subject;
an imaging device for obtaining the optical image formed by the optical system;
a case for enclosing the optical system and the imaging device;
a hermetic connector for hermetically sealing the case, the hermetic connector being electrically connected to the imaging;
an imaging-device holding member for holding the imaging device, the imaging-device holding member being disposed in the internal space of the case;
an optical-system holding member for holding the optical system so that the optical system is movable forward and backward along the optical axis relative to the imaging device, the holding member being disposed in the internal space of the case, the optical-system holding member having a slide contact surface which is slidable on the inner wall of the case, a protrusion on the outer surface of the optical-system holding member coming into contact with a contact portion on the inner wall of the case to restrict the forward movement of the optical-system holding member, and the rear end, including the protrusion of the optical-system holding member coming into contact with the imaging-device holding member to restrict the backward movement thereof along the optical axis;
a power generator for generating a driving force to move the holding member, the power generator being arranged in the case and generating a driving force based on an electric energy supplied thereto via the hermetic connector; and
a driving-force transfer member for connecting the power generator and the holding member to transfer the driving force of the power generator to the holding member.

12. The imaging system according to claim 11, wherein the power generator and the driving-force transfer member are disposed in the case.

13. The imaging system according to claim 12, wherein the power generator includes a motor unit, and the driving-force transfer member mechanically connects to the motor unit to transfer torque of the motor unit.

14. The imaging system according to claim 12, wherein the power generator includes a piezoelectric unit, and the driving-force transfer member mechanically connects to the piezoelectric unit to transfer the expansion and contraction of the piezoelectric unit.

15. The imaging system according to claim 11, wherein the holding member and the imaging device holding member for holding the imaging device are connected through a retractable elastic member to constitute the case.

16. The imaging system according to claim 15, wherein the power generator and the driving-force transfer member are disposed in the case.

17. The imaging system according to claim 15, wherein the elastic member restricts the forward or backward movement of the optical-system holding member along the optical axis.

18. The imaging system according to claim 17, wherein the power generator includes a piezoelectric unit, and the driving-force transfer member mechanically connects to the piezoelectric unit to transfer the expansion and contraction of the piezoelectric unit.

19. An imaging system comprising:
an optical system for forming an optical image of a subject;
an imaging device for obtaining the optical image formed by the optical system;
a case for enclosing the optical system and the imaging device;
an imaging-device holding member for holding the imaging device, the imaging-device holding member being disposed in the internal space of the case
an optical-system holding member for holding the optical system, the optical-system holding member being disposed in the internal space of the case, the optical-system holding member having a slide contact surface which is slidable on the inner wall of the case, a protrusion on the outer surface of the optical-system holding member coming into contact with a contact portion on the inner wall of the case to restrict the forward movement of the optical-system holding member, and the rear end, including the protrusion, of the optical-system holding member coming into contact with the imaging-device holding member to restrict the backward movement thereof along the optical axis;
a hermetic connector for hermetically sealing the case, the hermetic connector being electrically connected to the imaging device;
a holding member for holding the optical system so that the optical system is movable forward and backward along the optical axis relative to the imaging device, the holding member being arranged in the case;

a power generator for generating a driving force to move the holding member on the basis of electric energy which is supplied through the hermetic connector, the power generator being arranged in the case; and a driving-force transfer member for connecting the power generator and the holding member to transfer the driving force of the power generator to the holding member.

* * * * *